July 31, 1956 H. M. TIRET Plant Pat. 1,502
FUCHSIA PLANT
Filed Sept. 29, 1955
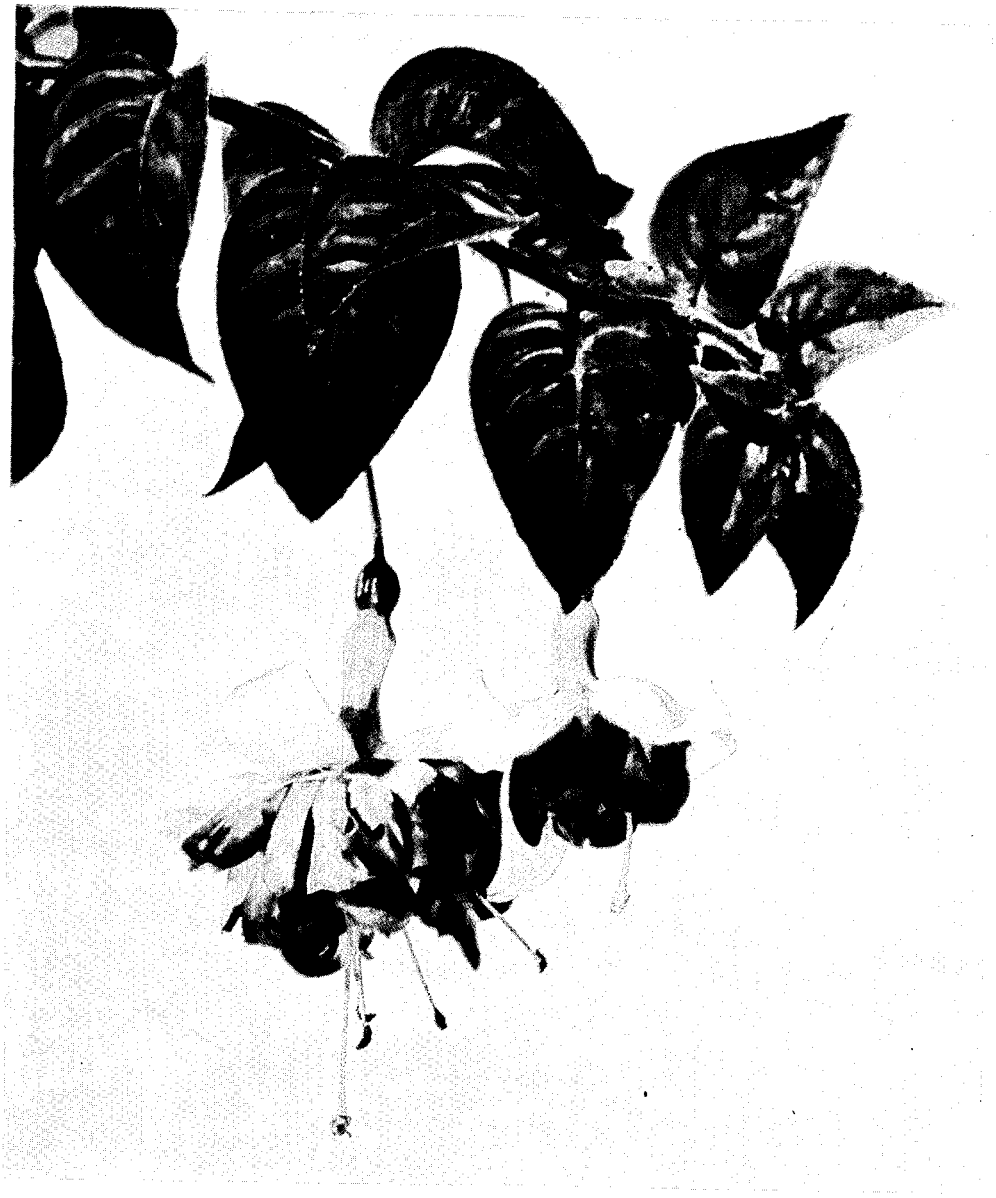

United States Patent Office

Plant Pat. 1,502

Patented July 31, 1956

1,502

FUCHSIA PLANT

Horace M. Tiret, San Francisco, Calif.

Application September 29, 1955, Serial No. 537,613

1 Claim. (Cl. 47—60)

This invention relates to a new and improved fuchsia plant, the principal new and different characteristic of which is the appearance of having three distinctly different flowers on the same bush at the same time.

The accompanying color photograph illustrates the plant in bloom and the aforementioned new and different characteristic.

The plant was derived as a hybrid from a seedling (unpatented) not introduced to the trade, namely, 3–39–18 (female), the figures representing applicant's own breeding symbols, and a seedling (unpatented) not introduced to the trade, namely, 5–43–1 (male). The fuchsia plant is distinguished principally by its three stages of development, wherein it is different in color at each of such stages. When the flower first opens, it is very deep in color, with white sepals, then the sepals become faintly shaded with pink tone of China Rose, with the corolla fading into a lighter color with slight marbling effect, culminating in a fully open sepal effect, pink in color and with petals very widespread. The fully open flower is exceptionally large. The resulting effect is one not previously existing in any other fuchsia plant. The plant has been asexually reproduced at Palo Alto, California, by cuttings which retained the characteristics of the parent fuchsia plant.

The plant may be trained equally well as a trailer or for upright growth, and grows vigorously in either manner. The branches form close together and dense, which is also characteristic of the flowers. In full bloom, the main petals, in the outer area, are colored Mallow Purple (British Horticultural Color Chart No. 630), while the inner area toward the base is colored Mallow Purple (British Horticultural Color Chart No. 630–3). When the flower first opens, the main petals are Mallow Purple (British Horticultural Color Chart 630–3) at the base, becoming deeper in color at the outer area, Spectrum Violet (British Horticultural Color Chart 735–1). The outer petals surrounding the main petals are splotched with Persian Rose (British Horticultural Color Chart 628–3), otherwise being similar in color to the main petals. The tube and sepals are flesh colored when the flower opens, and, as the flower matures, the sepals become shaded with pink tone of China Rose (British Horticultural Color Chart 024–3 to 024–1). The flower has no fragrance and is an early bloomer.

In the accompanying drawing, the figure shows a typical branch tip, the drawing representing approximate actual size.

A detailed description of this new variety of fuchsia plant follows:

*Habit of growth.*—Strong variety which may be trained either as an upright or trailer, whose branches in either event are dense and close together, and whose flowers are likewise close together.

*Foliage.*—The foliage is average medium large and dark green in color. The branches are dark red. The mature leaf is approximately 2¾″ in length and 1¾″ wide at the widest part. The leaves are lightly veined and the serrated edge is not pronounced. The outer surface is fairly smooth, with a slight crinkly appearance. The under side of the leaf is a lighter green than the top side.

*Flower.*—The flower has three stages of development and is different in color at each of those stages. At the first stage, when the flower opens, it is very deep in color with light sepals. At the next stage, the sepals are slightly pink, with the corolla fading into light color, showing slight marbling effect. When fully opened, the sepals become more pink and the petals spread out widely, affording a pronounced marbling effect. Fully opened, the flower is exceptionally large. At the fully opened stage, the main petals are colored Mallow Purple (British Horticultural Color Chart No. 630), the inner area toward the base is Mallow Purple (British Horticultural Color Chart 630–3). The outer petals surrounding the main petals are splotched with Persian Rose (British Horticultural Color Chart 628–3), otherwise the color of the petals is similar to that of the main petals.

*Petals.*—Approximately twenty-seven petals occur to each flower, appearing in a large, loose, and flaring open form. The diameter of the open, mature flower is approximately 3″, and each of the large petals is approximately 1½″ by 1½″ at the widest point. The color of the petals is as described above.

*Ovary.*—Pea green in color, length approximately ⅝″, width at widest point approximately ⅜″, measured at maturity.

*Tube.*—Pale green on the immature flower, becoming the same color as the sepals at maturity. The tube is long and narrow, being approximately 1″ in length, and 5/16″ in width, at the widest point, measured at maturity.

*Sepals.*—The sepals are four in number, approximately 1¾″ long and ⅞″ wide at the widest point, measured at maturity. In form the sepals are broad and fully recurved when the flower is at maturity. The under side has a satiny appearance and crepe-like texture, while the outer side is satiny in appearance with the smoother texture.

*Pistil.*—The style is approximately 3¾″ in length, and 1/16″ in width, measured at maturity. The style is white in color, and the stigma is a yellowish green.

*Stamens.*—The stamens are eight in number, colored pink with plum-colored anthers. They are 2¼″ in length, measured at maturity, and very slender.

*Parentage.*—Applicant's own seedling (unpatented) not introduced to the trade, applicant's breeding symbols 3–39–18 (female) and 5–43–1 (male).

It is noted that the foliage and flowers will vary somewhat with the seasons and growing conditions; however, the fuchsia plant is thoroughly differentiated from others by reason of the three distinct stages of development, with a difference of color at each stage, and the appearance of three different flowers simultaneously on the same plant.

Having thus disclosed my discovery, I claim:

The new and distinct variety of fuchsia plant herein described and illustrated characterized by the three distinct stages of development and the effect of three different flowers growing simultaneously on the same plant.

No references cited.